United States Patent
Krebs et al.

[11] Patent Number: 5,926,685
[45] Date of Patent: *Jul. 20, 1999

[54] METHOD OF MAKING AN ORTHOPAEDIC IMPLANT HAVING A POROUS SURFACE USING AN ORGANIC BINDER

[75] Inventors: Steve Krebs, Fort Wayne; Clarence Panchison; H. Ravindranath Shetty, both of Warsaw, all of Ind.

[73] Assignee: Zimmer, Inc., Warsaw, Ind.

[*] Notice: This patent is subject to a terminal disclaimer.

[21] Appl. No.: 09/007,033

[22] Filed: Jan. 14, 1998

Related U.S. Application Data

[63] Continuation of application No. 08/542,230, Oct. 12, 1995, Pat. No. 5,734,959.

[51] Int. Cl.⁶ ................................................ B22F 3/10
[52] U.S. Cl. .................................................. 419/2; 419/37
[58] Field of Search ................................... 419/2, 37

[56] References Cited

U.S. PATENT DOCUMENTS

| | | | |
|---|---|---|---|
| 4,612,160 | 9/1986 | Donlevy et al. | 419/2 |
| 4,964,907 | 10/1990 | Kiyota et al. | 75/235 |
| 5,080,672 | 1/1992 | Bellis | 623/16 |
| 5,098,870 | 3/1992 | Claar et al. | 501/87 |
| 5,443,510 | 8/1995 | Shetty et al. | 419/2 |
| 5,498,302 | 3/1996 | Davidson | 148/317 |
| 5,535,810 | 7/1996 | Compton et al. | 164/35 |
| 5,549,700 | 8/1996 | Graham et al. | 623/22 |
| 5,571,187 | 11/1996 | Devanathan | 623/16 |
| 5,734,959 | 3/1998 | Krebs et al. | 419/2 |
| 5,758,253 | 5/1998 | Teoh et al. | 419/2 |

*Primary Examiner*—Daniel J. Jenkins
*Attorney, Agent, or Firm*—Todd A. Dawson

[57] ABSTRACT

The invention is directed to a method of forming an implant having a porous surface using an organic binder compound to enhance the bonding between the porous surface layer and implant. Preferably, the binder is formed from a water-soluble protein that carbonizes during the sintering process to alloy with the metal of the porous surface layer. The porous surface layer may be in the form of beads or of fiber metal and can be preformed to fit with an implant or formed over the surface of the implant.

14 Claims, 3 Drawing Sheets

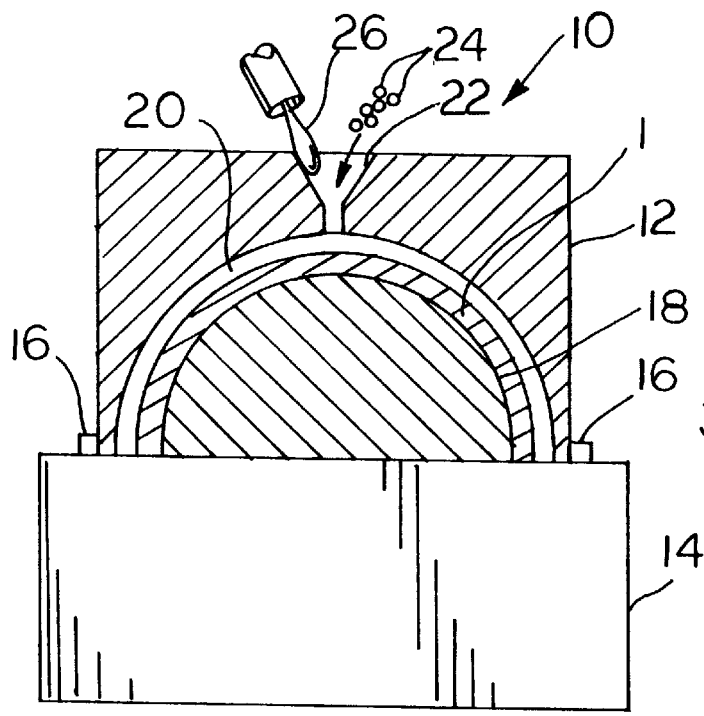
FIG.1
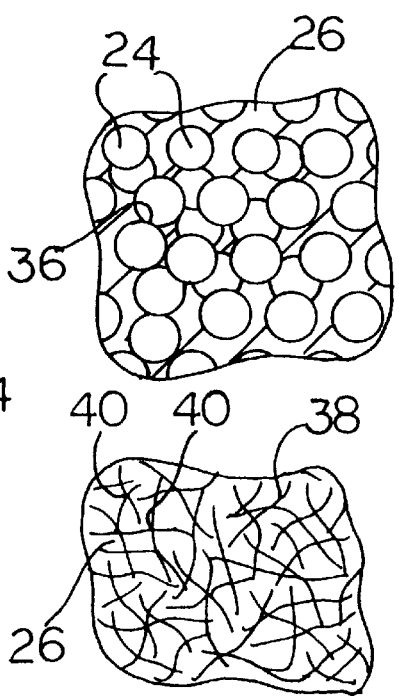
FIG.3
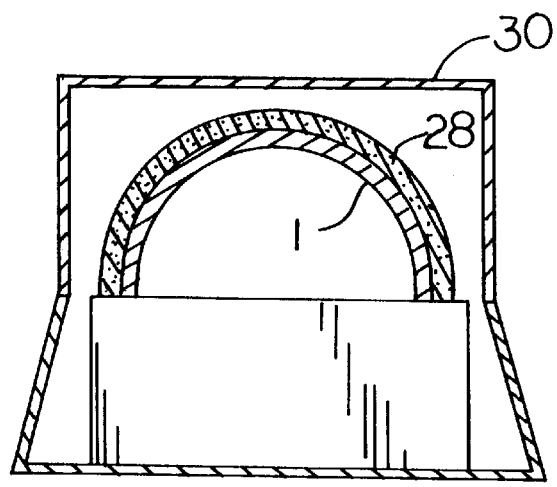
FIG.2
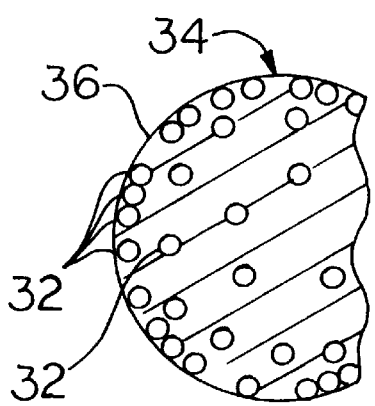
FIG.4
FIG.5

METHOD OF MAKING AN ORTHOPAEDIC IMPLANT HAVING A POROUS SURFACE USING AN ORGANIC BINDER

This application is a continuation of U.S. Patent application Ser. No. 08/542,230 filed Oct. 12, 1995, now U.S. Pat. No. 5,734,959.

BACKGROUND OF THE INVENTION

1. Field of the Invention

The present invention relates to orthopaedic implants and, more particularly, to a method of making orthopaedic implants having a porous surface connected thereto by a process utilizing an organic binder compound.

2. Description of the Related Art.

Orthopaedic implants of known design may be constructed, e.g., of cobalt-chromium-molybdenum or titanium. Such materials provide suitable physical characteristics of strength, corrosion resistance, wear properties and biocompatability for use in orthopaedic applications.

It is also known to provide an orthopaedic implant with a porous surface at the exterior thereof The porous surface may be used to promote bone ingrowth and thereby enhance implant fixation within the bone. Alternatively, the porous surface may receive bone cement therein to enhance implant fixation within the bone. Such porous surfaces may be constructed, e.g., of metal beads or fiber metal mesh which are sintered, diffusion bonded or welded to the implant to form an integral part of the implant.

Presently, fiber metal mesh used to form a porous surface is pressed into a desired shape and maintained under pressure during the sintering process in which some of the fibers are bonded together to form a pad. The process may also be referred to as diffusion bonding. The metal pad is shaped to correspond to its supporting surface and is then positioned in contact with an implant and clamped in place during a sintering process. Alternatively, the fiber metal pad may be gravity sintered, thereby eliminating the use of external clamping forces. A similar process may be employed when making a porous surface using metal beads.

Sintering the porous surface layer to the implant with external pressure is time consuming and expensive for the manufacturer. During sintering, the ramp up and cool down time for the furnace is approximately 14 hours per cycle. If the porous surface layer is being connected, for example, to the interior bone engaging surface of a femoral knee component, it may take 4 complete cycles. The complex geometric interior design of the femoral knee component requires that only one or two pads be attached during one cycle. The typical interior of the femoral knee defines 5 distinct surfaces which require a porous coating. Therefore, to completely bond all of the porous surface layers to the interior of the femoral knee component would require in excess of 56 hours of furnace time. Added to that time is the time required to connect the clamp tooling to the implant for holding the pad in contact with the implant. From the above description, it is clear that providing a porous surface layer on an implant using existing technologies is time consuming and expensive for the manufacturer of orthopaedic implants.

SUMMARY OF THE INVENTION

The present invention provides a method of making an orthopaedic implant having a porous surface by utilizing a water-soluble protein compound such as gelatin to enhance bonding of the porous surface to the implant. Preferably, the gelatin includes an alloying element that is diffused into the metallic particles and lowers the melting temperature of the metallic particles at the interface surfaces by raising the carbon content at the surface of the metal particles. Alternatively, the porous surface layer could be fiber metal mesh impregnated with or otherwise coated by the gelatine. If the porous surface is formed from the plurality of metal wires or fiber metal mesh as it is commonly known, the process includes forming a pad of fiber metal and then impregnating the pad with the gelatine binder. The impregnated pad is then placed in contact with an implant and then gravity sintered.

Regardless of whether the porous layer is formed from a plurality of beads or a layer of fiber metal mesh wire during sintering and presintering, the binder exhibits specific temperature dependant phases. Initially, after the binder is coated over the porous surface layer, or after the impregnated porous layer is applied to the implant, the implant, porous layer, and binder are allowed to dry. Drying causes the binder to become very hard and forms an initial temporary bond between the porous layer and the implant. As the furnace ramps up in temperature, the binder forms a carbon frame-work with the thin porous layer and implant. As the temperature of the furnace continues to increase, some of the carbon becomes defused into the surface of the wires making up the fiber metal mesh. The increased carbon content of the wires decreases the melt temperature of the wires at their surface and causes the wires to fuse or melt bond at contact points with other wires or the implant. Further, if the wires are not in direct contact, the carbon frame work formed by the binder may assist the melting metal to bridge. Eventually, all of the carbon is defused into the wire and the volatile constituents in the binder are removed leaving the resultant implant substantially free from binder debris. By using the binder and method of the current invention, all the porous surfaces may be connected to the implant at the same time. As the binder dries and hardens, the binder alone is sufficient to hold the porous surface layers in contact with the implant. Therefore, only one furnace cycle is required to bond a plurality of porous surface layers to the implant. Further, since the binder lowers the melting point of the surface of the wires making up the fiber metal mesh, sintering can be completely accomplished in a shorter sintering cycle and at a lower temperature. Finally, since the binder forms melt bridges between adjacent and the contacting fibers, the bonding within the porous layer is more complete.

In another version of the invention, a plurality of metallic particles are mixed with a water-soluble protein mixture and are spread over the surface of an implant to form a beaded porous surface layer for the implant. For instance, the beads and binder may be poured into a mold to form an outer porous shell of an acetabular cup. The shell is attached to a body of an orthopaedic implant as by sintering or the shell may be sintered separately and placed within an injection mold device to form the outer porous surface of a injection molded polyethylene cup.

In yet another variation of the invention, the binder is used to secure a layer of fine beads to the surface of a fiber metal pad. The fine layer of beads provides a greater contact surface for later sintering the pad to the implant using the binder. This variation could be accomplished by spreading a layer of small bead along the implant surface and then overlying the layer of beads with a layer of fiber mesh. The fiber mesh and beads could then be coated or impregnated with the binder material and then processed according to the teachings set forth above. Alternatively, the bead/fiber metal combination could be presintered together utilizing the binder method of the above invention and then sintered as a unit to the implant, again using the teachings of the subject application. The value of the combination of fiber metal and small beads as described resides in the increased surface area to contact and bond with the implant yet provides the porous fiber metal mat for contact with bone or cement.

While it is believed that the binder alone will be adequate to hold the porous surface layer against the implant, there may be instances or areas on the implant when it may be advantageous to spot weld the pad to the implant to provide initial fixation prior to sintering.

In all variations of the invention it is important that the binder be formed from a protein compound such as gelatine. Gelatine is especially attractive as a binder agent due to its ease of use in a manufacturing environment. The gelatine binder is easy to apply as it does not require any special handling equipment, and it is non-toxic and otherwise safe to handle. Furthermore, if the gelatine is applied incorrectly, it can be washed off with warm water without any damage to the implant or porous surface.

An advantage of the present invention is that external forces (and associated machinery) are not required to hold the porous layer to the implant during the sintering operation.

Yet another advantage is that the binder is in the form of a protein mixture which converts to carbon during the debinding and presintering operation.

A further advantage is that the binder may include an alloying material which is diffused into the metallic particles, thereby lowering the melting point at the interface surfaces of the metallic particles which is less than the melting point of the material from which the metallic particles are initially constructed.

Still further advantages of the invention will become apparent upon a reading of the following description taken with the accompanying drawings.

BRIEF DESCRIPTION OF THE DRAWINGS

The above-mentioned and other features and advantages of this invention and the manner of attaining them will become more apparent and the invention will be better understood by reference to the following description of embodiments of the invention taken in conjunction with the accompanying drawings, wherein:

FIG. 1 is a side, sectional view of an embodiment of a mold assembly used in the method of the present invention illustrating a shell of metal beads and binder being poured onto and molded over a metal acetabular cup;

FIG. 2 is a side, sectional view of the shell of FIG. 1 disposed within an embodiment of a diagrammatically illustrated furnace;

FIG. 3 is a fragmentary view of a shell molded with the mold in FIG. 1, including beads and a binder;

FIG. 4 is a fragmentary view of a shell molded with the mold in FIG. 1, including metal fibers and a binder; and FIG. 5 is a cross-sectional diagrammatical view of a bead shown in FIG. 3, illustrating a high carbon content of alloying material at the surface of the bead after a sintering process, illustrated in FIG. 2, is complete.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 6:
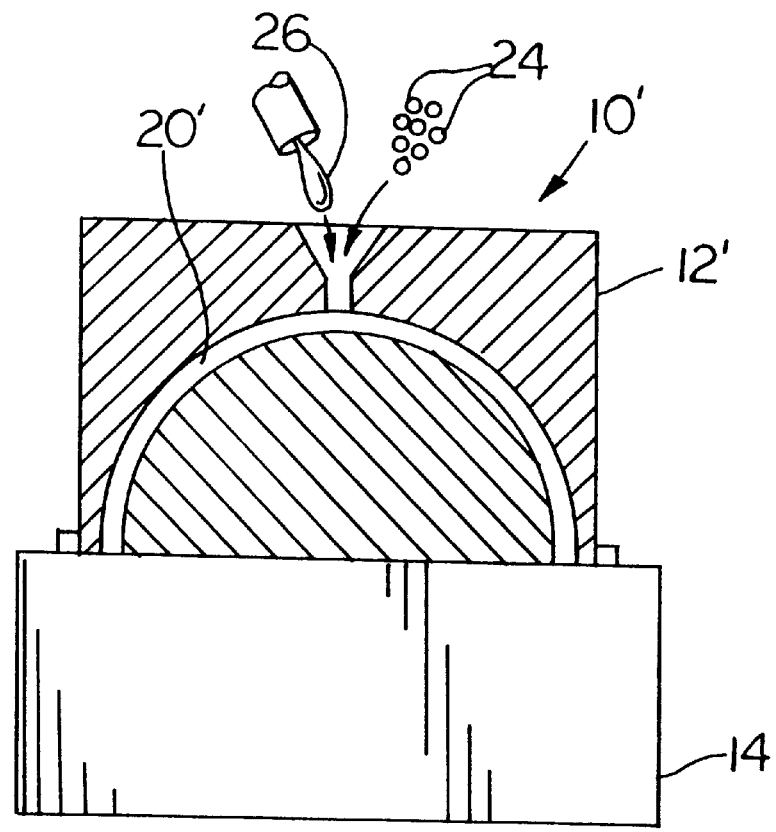
FIG. 6 is a side, sectional view of an embodiment of a mold assembly used in the method of the present invention.

Referring now to the drawings, and particularly to FIG. 1, there is shown an embodiment of a mold assembly 10 which can be utilized to form a porous surface on the outer surface of an orthopaedic implant. Mold assembly 10 generally includes a first mold half 12 and a second mold half 14. Second mold half 14 includes a flange 16 for positioning first mold half 12 relative thereto. Further, second mold half 14 includes a contoured surface 18 which is either integral with or separably associated with second mold half 14. As illustrated, second mold half 14 is configured to accommodate and otherwise support a metal acetabular cup 1. It should be understood that while an acetabular cup is illustrated, this should not be considered a limitation on the invention. For example, the invention could apply equally to the fixation of a porous layer to the exterior surface of a femoral hip stem implant, or femoral knee joint component with the molds altered respectively. As another example, contoured surface 18 may be in the form of a prosthetic implant which is separately associated with second mold half 14.

First mold half 12, with acetabular cup 1 supported thereon, and contoured surface 18 of second mold half 14 define a mold cavity 20 therebetween. Mold cavity 20 is in communication with an inlet 22 which is sized and configured for receiving metallic particles 24 therein. Metallic particles 24 may be in the form of metal beads. Inlet 22 is also adapted to receive a binder therein, such as a water-soluble protein mixture 26. In the embodiment shown in FIG. 1, protein mixture 26 is in the form of gelatin 26 having an alloying material (to be discussed hereinafter) therein. Gelatin 26 is preferably suspended in water at a concentration between 0.10% to 50% by weight. Glycerin may also be added to the gelatin mixture as a plasticizer. In a preferred embodiment, the gelatin mixture consists essentially of 10 ml of water, 0.75 grams gelatin, and 0.02 to 0.05 grams glycerin.

During use, metallic particles 24 and gelatin 26 may be mixed together and introduced into mold cavity 20, such that the mixture substantially and entirely fills mold cavity 20 about the outer surface of acetabular cup 1. Mold cavity 20 is configured to form a shell about the cup having a desired shape with the mixture of metallic particles 24 and gelatin 26. After the mixture fills the mold cavity, gelatin 26 is allowed to set-up or harden within mold cavity 20. Alternatively, the mixture, mold and implant may be frozen to allow the mold halves to be separated and the implant removed. In either instance, the implant with the gelatine and bead mixture adhered thereto is allowed to dry for a period of time. Drying causes the gelatine to become very hard.

After drying, implant 1 with shell 28 adhering thereto is placed within a furnace 30 shown in simplified form in FIG. 2. Furnace 30 provides the dual functionality of both converting the gelatin mixture substantially to carbon, and bonding metallic particles 24 together via sintering. More particularly, after shell 28 is place within furnace 30, the air within furnace 30 is evacuated using a pump or other suitable mechanism (not shown) down to a pressure of $1\times10^{-5}$ TORR pressure. Furnace 30 is thereafter backfilled by pumping an inert gas such as high purity argon therein to a pressure zero (0) PSIG. Subsequently, furnace 30 is again evacuated by pumping the high purity argon within furnace 30 down to a pressure of $1\times10^{-5}$ TORR. This evacuating and backfilling process is repeated two additional times and furnace 30 is thereafter backfilled with high purity argon to a partial pressure of at least 100 micrometers. Reactive gases such as nitrogen, hydrogen and mixture of nitrogen and hydrogen gas can also be used in the process. The temperature within furnace 30 is then increased at a rate of 25° F. per minute to a predetermined temperature of 1,000° F. and held at this temperature for 15 minutes. Furnace 30 is then heated again at a rate of 20° F. per minute to a sintering temperature of 2,350° F. and held at this temperature for a time period of between 15 minutes to 8 hours which is effective for carrying out a sintering process which provides an implant having a suitable bead bond strength for a particular application. It is anticipated that the preferred cycle time will be approximately 2 hours.

In the embodiment shown in FIGS. 1 and 2, metallic particles 24 and gelatin 26 are mixed prior to delivery within mold cavity 20. However it is to be understood that metallic particles 24 can be introduced into mold cavity 20, and gelatin 26 can thereafter be injected into mold cavity 20.

When shell 28 is disposed in furnace 30 and the temperature therein is increased at the predetermined rate as described above, at a temperature around 1300 degrees Fahrenheit the gelatin mixture within shell 28 is converted essentially into residual carbon which then covers metallic particles 24. The carbon defines an alloying material which is diffused into metallic particles 24 from which metallic particles 34 are made (FIG. 5). Further, as the furnace temperature ramps up, all volatile constituents in the binder are removed leaving only the carbon. For example, FIG. 5 illustrates a fragmentary, sectional view of a metal bead after the diffusion of carbon 32 therein from the binder as described above to form metal bead 34. Since the gelatine contacts only the periphery of the bead, carbon 32 may be disposed at a higher concentration about the periphery 36 of metal bead 34, as shown (FIG. 5). The carbon illustrated deeper within the bead represents carbon already present in the bead. Carbon 32 within alloyed metal bead 34 results in a lower melting point at the interface surface (e.g., periphery) of alloyed metal bead 34. That is, the eutectic composition of alloyed metal bead 34 having carbon 32 therein results in an interface surface 36 having a eutectic melting point which is less than the melting point of the Co—Cr—Mo alloy from which alloyed metal bead 34 is initially constructed. The sintering process takes place at a temperature which is less than the eutectic melting point of alloyed bead 34, which in turn is less than the melting point of the Co—Cr—Mo alloy from which alloyed metal bead 34 is constructed.

In the embodiment shown in FIG. 5, the alloying material within alloyed metal bead 34 is in the form of carbon 32, as described above. However, it is also possible that the alloying material can be in the form of silicon, ferrosilicon, F-75 alloy, and/or iron. Such alloying materials are typically in the form of a powder which is suspended within gelatin 26 (FIG. 1).

Referring now to FIG. 3, an enlarged, fragmentary view of shell 28 shown in FIG. 2 is illustrated prior to carbonization of gelatin 26. Metallic particles 24 are in the form of metal beads 24 which are held together using gelatin 26. Metal beads 24 may contact adjacent metal beads 24 along respective interface surfaces 36 (FIGS. 3 and 5).

Referring now to FIG. 4, an enlarged, fragmentary view of an alternate embodiment of a shell is shown. A metal layer is partially illustrated formed from metallic metal mesh as is well known in the industry. The metal mesh is formed from a plurality of metal fibers 38 which are in contact with each other at respective interface surfaces 40. Metal fibers 38 are held in place prior to sintering using gelatin 26 (FIG. 1) which has been allowed to set-up.

Figure 7:
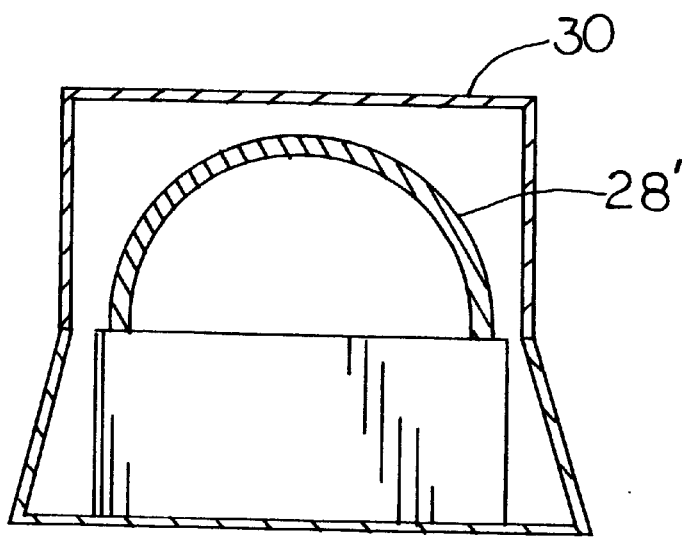
FIG. 7 is a side, sectional view of a shell molded with the mold of FIG. 6, and disposed within an embodiment of a diagrammatically illustrated furnace.

In the embodiments described above, metallic particles 24 and binder 26 are introduced within mold cavity 20 of mold assembly 10. However, it is also to be understood that a mixture of metallic particles 24 and binder 26 can be manually applied to an orthopaedic implant surface, such as a contoured surface 18 shown in FIG. 1. Further, it is also possible to use a mixture of metallic particles 24 and binder 26 within a compression molding and/or injection molding machine to form a shell 28'. As illustrated in FIG. 6, a shell 28' is formed using a mold 10' having an upper mold portion 12 and a lower mold portion 14. A mold cavity 20' is formed between the upper and lower mold portions and may be filled with metal beads 24 and binder 26. After molding, the shell 28' is dried and then sintered in oven 30 (FIG. 7) to form a rigid porous shell. The rigid porous shell 28' is may then be placed in an injection mold machine to form the porous backing for a molded acetabular cup.

Figure 8A:
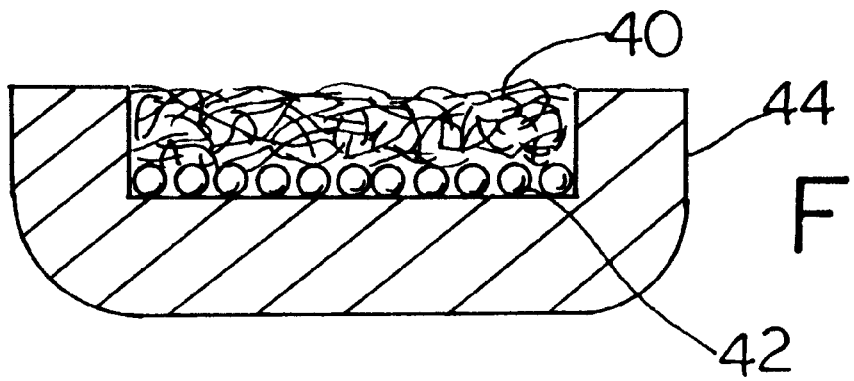
FIG. 8A is a side sectional view of an implant having a porous surface layer formed consistent with the invention and including a layer of metal beads between the implant and a layer of fiber metal mesh.
Figure 8B:
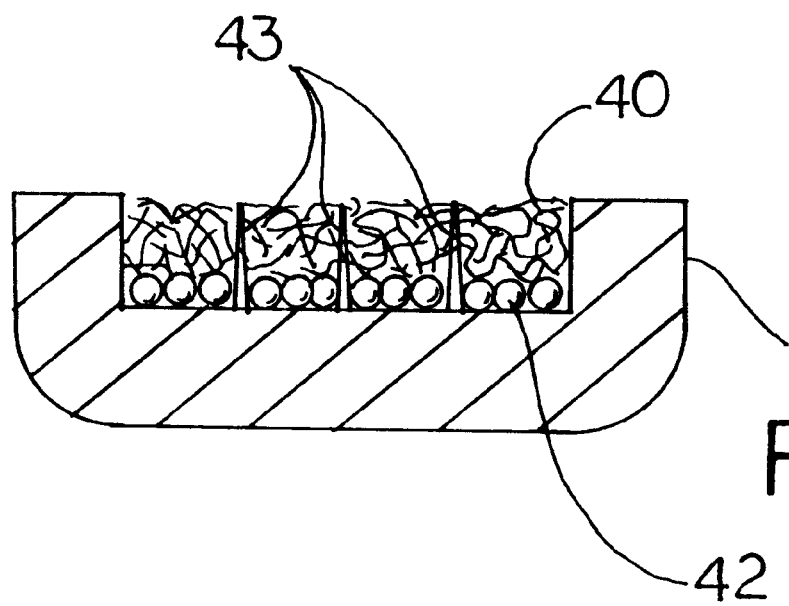
FIG. 8B is a side sectional view of an implant having a porous surface layer formed consistent with the invention and including a plurality of spot welds to hold the porous layer in position prior to sintering.

A further example of the usefulness of the binder method of this invention is illustrated in FIG. 8A wherein a fiber metal mesh pad 40 is connected to an implant 42 via a layer of small beads 44. In use, the beads 44 are layered on the implant and the fiber mesh is supported by the layer of beads. The beads and mesh are coated or impregnated with the binder. The binder and implant are processed in a manner consistent with the above method. During sintering, the small beads are bonded to the fiber mesh and to the implant. Alternatively, several spot welds 43 (preferably formed by a laser welder) may be used (FIG. 8B) to fix the metal pad 40 and beads 44 in place on the implant 42 prior to sintering. The advantage of such a construction would be two fold. First, the bead would present a greater surface area and thereby bond better with the implant as compared to fiber metal. Second, the fiber metal is believed to form a better area for the ingrowth of bone as compared to the beads.

Figure 9:
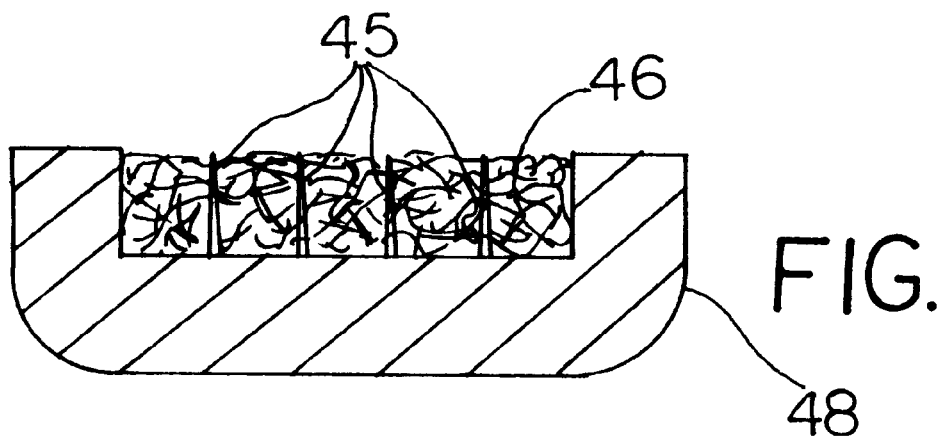
FIG. 9 is a side sectional view of an implant having a porous surface layer formed consistent with the invention and including a plurality of spot welds to hold the porous layer in position.

While it is believed that the binder will, when dry, adequately hold a layer of fiber metal mesh to the implant during sintering, FIG. 9 illustrates a potential variation of the method of the invention. In the embodiment of FIG. 9, after the fiber metal is positioned on the implant, several spot welds 45 are made to fix the metal mesh 46 to the implant 48 prior to sintering. Either before or after the spot welding, the metal mesh is impregnated with the binder material consistent with the above description.

It has been found that if cobalt-chromium-molybdenum metallic beads 24 are used which have an initial concentration of 0.24 to 0.26% carbon, the final carbon content within metal beads 34 (FIGS. 3 and 5) using the process of the present invention is approximately 0.31%. It is therefore possible to vary the final carbon content within metal beads 34 by varying the initial carbon concentration within metal beads 34 and the concentration of carbon within gelatin 26.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of forming a porous surface for use with an orthopaedic implant, said method comprising the steps of:

providing a plurality of metallic particles;

mixing a water-soluble protein compound with said metallic particles; and forming a shell having a desired shape with said mixture of metallic particles and water-soluble protein compound.

2. The method of claim 1 comprising the further steps of:

providing a mold having a mold cavity; and introducing said metallic particles into said mold cavity.

3. The method of claim 2, wherein said introducing step occurs prior to said mixing step.

4. The method of claim 2, wherein said introducing step occurs after said mixing step.

5. The method of claim 2, wherein said forming step comprises allowing said shell to harden within said mold cavity, said method comprising the further steps of:

removing said hardened shell from said mold cavity;

placing said hardened shell within a furnace; and bonding said metallic particles together.

6. The method of claim 5, comprising the further steps of:

evacuating air from said furnace, such that a low pressure exists within said furnace;

pumping a gas into said furnace; and increasing the temperature within said furnace at a predetermined rate per unit of time;

said evacuating, pumping and increasing steps occurring prior to said bonding step.

7. The method of claim 5, wherein said bonding step comprises one of diffusion bonding and sintering.

8. The method of claim 1, wherein said metallic particles comprise at least one of metal fibers and metal beads.

9. The method of claim 1, wherein said water-soluble protein compound comprises gelatin.

10. The method of claim 1 wherein said shell is formed about an exterior surface of a metal acetabular cup.

11. A method of forming a porous surface for use with an orthopaedic implant, said method comprising the steps of:

providing a plurality of metal particles;

mixing a water-soluble protein binder with said metalic particles;

forming a shell having a desired shape with said mixture of metallic particles and water-soluble protein binder;

increasing the temperature within said furnace such that said water-soluble protein binder converts essentially to residual carbon;

further increasing the temperature within the furnace to a predetermined temperature which is less than a melting point of said metallic particles; and sintering said metallic particles together at said predetermined temperature.

12. The method of claim 11, comprising the further step of diffusing at least a portion of said residual carbon into said metallic particles.

13. The method of claim 11, comprising the further steps of:

evacuating air from said furnace, such that a low pressure exists within said furnace; and pumping an gas into said furnace;

said evacuating and pumping steps occurring prior to said sintering step.

14. A method of increasing the carbon content of a metal, the method including the steps of:

providing a metal having a predetermined quantity of carbon;

applying a binder to the metal, the binder being a water soluble binder material having an alloying material therein, placing the binder and the metal in a furnace and raising the temperature of the furnace until the binder converts essentially to carbon; and further increasing the temperature within the furnace to a predetermined temperature which is less than a melting point for the metal.

* * * * *